(12) United States Patent
Dukhin et al.

(10) Patent No.: US 6,910,367 B1
(45) Date of Patent: Jun. 28, 2005

(54) METHOD FOR DETERMINING PARTICLE SIZE DISTRIBUTION AND STRUCTURAL PROPERTIES OF CONCENTRATED DISPERSIONS

(75) Inventors: Andrei Dukhin, Goldens Bridge; Philip J. Goetz, Mt. Kisco, both of NY (US)

(73) Assignee: Dispersion Technology, Inc., Bedford Hill, NY (US)

(*) Notice: Subject to any disclaimer, the term of this patent is extended or adjusted under 35 U.S.C. 154(b) by 563 days.

(21) Appl. No.: 09/693,052

(22) Filed: Oct. 23, 2000

(51) Int. Cl.[7] ............................................... G01N 5/02
(52) U.S. Cl. .................... 73/61.75; 73/61.79; 73/865.5; 73/61.41
(58) Field of Search ............................... 73/61.75, 61.79, 73/865.5, 69.53, 53.01, 61.41, 61.42, 61.43, 61.44, 61.45, 61.46, 61.76, 597, 599, 61.71

(56) References Cited

U.S. PATENT DOCUMENTS

| | | | | | |
|---|---|---|---|---|---|
| 4,571,693 | A | * | 2/1986 | Birchak et al. ............. | 73/24.01 |
| 5,285,675 | A | * | 2/1994 | Colgate et al. .............. | 73/23.2 |
| 5,551,282 | A | * | 9/1996 | Van der Heyden ......... | 73/30.03 |
| 6,119,510 | A | * | 9/2000 | Carasso et al. ............. | 73/61.75 |
| 6,205,848 | B1 | * | 3/2001 | Faber et al. ................ | 73/61.75 |
| 6,209,387 | B1 | * | 4/2001 | Savidge ...................... | 73/24.05 |
| 6,216,091 | B1 | * | 4/2001 | Hammond ................... | 702/23 |

OTHER PUBLICATIONS

Dukhin et al. Langmuir, Sep. 1996, vol. 12, pp. 4987–5003.*
Dukhin et al. Langmuir, Jul. 1999, vol. 15, pp. 6692–6706.*
Hayashi et al. Journal of the Society of Powder Technology, Japan. Dec. 2000, vol. 37, No. 7, pp. 496–504.*
Chen et al. Journal of Colloid and Interfacial Science, Feb. 1991, vol. 141, No. 2, pp. 564–577.*
U.S. application No. 09/108,072, Dukhin et al., e US 6109098.
A.S. Dukhin and P.J. Goetz, "Acoustic Spectroscopy for Concentrated Polysisperse Colloidswith High Density", Langmuir., 12 (21) 4987–4997, 1996.) . Sepiombor 1996.
Dukhin, A.S., Shilov, V.N., Ohshima, H., Goetz, P.J. "Electroacoustics Phenomena in Concentrated Dispersions. New Theory and CVI Experiment", Langmuir, 15, 20, 6692–6706, 1999). Jul. 1999.
Hayashi, T., Ohya, H., Suzuki,S., Endoh, S., Errors in Size Distribution Measurement of Concentrated Alumina Slurry by Ultrasonic Attenuation Spectroscopy:, J.Soc. Powder Tech., Japan 498–504 (2000). Dec. 2000.
Lyklema, J. "Fundamentals of Interface and Colloid Science", Vol. 1, Academic Press, 1993.
Chen, M. and Russel, W.B. "Characteristics of Flocullated Silica Dispersions", J.Colloid Interface Sci., 141, 2, 564–577 (1991), Feb. 1991.

* cited by examiner

*Primary Examiner*—Hezron Williams
*Assistant Examiner*—Michael Cygan

(57) ABSTRACT

A method is described which applies Acoustic Spectrometry to characterize both the particle size distribution and microrheological properties of the structured concentrated dispersions. It suggests to model the structured dispersion as a collection of the spherical particles which are connected together with flexible strings. Oscillation of these strings creates an additional energy dissipation which contributes to the total attenuation. This dissipation is dependent on the second virial coefficient characterizing the flexibility of the strings. It is shown that the value of the second virial coefficient can be calculated from the measured attenuation spectra either for known particle size or together with particle size as adjustable parameter.

3 Claims, 5 Drawing Sheets

METHOD FOR DETERMINING PARTICLE SIZE DISTRIBUTION AND STRUCTURAL PROPERTIES OF CONCENTRATED DISPERSIONS

FIELD OF THE INVENTION

This invention relates to using the measured ultrasound attenuation spectra to determine not only the particle size distribution but importantly the characteristics of the inter-particles bonds in structured concentrated dispersions.

BACKGROUND OF THE INVENTION

This invention deals with a particular kind of dispersed system (or colloid) that can be described as a collection of small particles immersed in a liquid. These particles can be either solid (dispersions) or liquid (emulsions). Such dispersed systems play an important role in all kind of paints, lattices, food products, paper coatings, polymer solutions, etc.

These systems have a common feature. Because of the small particle size, the total surface area of the particles is large relative to their total volume. Therefore surface related phenomena determine their behavior in various processes. This invention has particular application to dispersed systems where these surface effects are dominant, corresponding to a range of particle size up to about 10 microns. The importance of these surface effects disappears for larger particles. (??? Structural losses might be important even if particles are large and surface phenomena not so important)

The characterization of such colloids is important not only for the manufacture, but also the development of new systems with improved properties. Particle size distribution is a one of the basic notions for characterizing these dispersed systems. Several methods are known for determining particle size. Most methods are based on light, for example: light scattering; light diffraction; etc. There is a new alternative method based on ultrasound that is rapidly becoming important. This ultrasound method has a large advantage over traditional light-based techniques because it is able to characterize a concentrated system without dilution. Light-based methods usually require extreme dilution in order to make the sample sufficiently transparent for measurement. This invention deals with improvements of this ultrasound characterization technique.

There are two methods for ultrasound characterization of disperse systems: Acoustics and Electroacoustics. This invention deals only with Acoustics.

This acoustic method involves two steps. The first step is to perform an experiment on the disperse system to obtain a set of measured values for certain macroscopic properties such as temperature, pH, attenuation spectra, sound speed, etc. This invention does not deal with this step, but rather assumes that such instruments for accurate and precise measurement of the ultrasound attenuation spectra and sound speed are available. One such instrument is described in the U.S. Patent by Dukhin, A. S. and Goetz, P. J. "Method and device for characterizing particle size distribution and zeta potential in concentrated system by means of Acoustic and Electroacoustic Spectroscopy", Ser. No. 09/108,072.

The second step is an analysis of the measured data to compute the desired microscopic properties such as particle size. Such an analysis requires three tools: a model dispersion, a prediction theory, and an analysis engine.

A "model dispersion" is an attempt to describe a real dispersion in terms of a set of model parameters including, of course, the desired microscopic characteristics. The model, in effect, makes a set of assumptions about the real world in order to simplify the complexity of the dispersion and thereby also simplify the task of developing a suitable prediction theory. For example, most particle size measuring instruments make the assumption that the particles are spherical and therefore a complete geometrical description of the particle is given by a single parameter, its diameter. Obviously such a model would not adequately describe a dispersion of carpet fibers that have a high aspect ratio and any theory based on this over-simplified model might well give incorrect results. The model dispersion may also attempt to limit the complexity of the particle size distribution by assuming that it can be described by certain conventional distribution functions, such as for example a lognormal distribution.

A "prediction theory" consists of a set of equations that describes some of the measured macroscopic properties in terms of these microscopic properties of the model dispersion. For example, a prediction theory for acoustics would attempt to describe a macroscopic property such as the ultrasound attenuation in terms of such microscopic properties as the particle size distribution, volume fraction of the dispersed phase and various physical properties of the particles and liquid.

An "analysis engine" is essentially a set of algorithms, implemented in a computer program, that calculates the desired microscopic properties from the measured macroscopic data using the knowledge contained in the prediction theory. The analysis can be thought of as the opposite or inverse of prediction. Prediction describes some of the measured macroscopic properties in terms of the model dispersion. Analysis, given only the values for some of the model parameters, attempts to calculate the remaining properties by an analysis of the measured data. There are many well-documented approaches to this analysis task.

In our previous invention U.S. Patent by Dukhin, A. S. and Goetz, P. J. "Method and device for characterizing particle size distribution and zeta potential in concentrated system by means of Acoustic and Electroacoustic Spectroscopy", Ser. No. 09/108,072 we considered dispersions where the only particle/particle interaction was hydrodynamic in nature. That is, one particle that moves also disturbs its neighboring particles by means of hydrodynamic forces. This assumption was reflected in the corresponding "model dispersion" which neglects the possibility of any other type of particle interaction, for instance, polymer bridges.

In this patent we extent acoustic spectroscopy to the "structured dispersions" where particles are not separate. As a result we use a different "model dispersion" adding particle-particle links as a flexible strings.

In turn, the new "model dispersion" requires the new "prediction theory" and "analysis engine" which are given in this patent as well.

Measurement part is exactly the same as in our previous invention U.S. Patent by Dukhin, A. S. and Goetz, P. J. "Method and device for characterizing particle size distribution and zeta potential in concentrated system by means of Acoustic and Electroacoustic Spectroscopy", Ser. No. 09/108,072

BRIEF SUMMARY OF INVENTION

The applicant describes a new method of calculating the particle size distribution from measured attenuation spectra, which is not only valid in structured concentrated dispersions, but importantly yields additional information about the structure or particle-particle interactions as for example in the case of polymer bridging, double layer overlap, or simple mechanical entrapment of one particle by another.

BRIEF DESCRIPTION OF THE DRAWINGS

Table 1. Particle size of the two alumina samples

DETAILED DESCRIPTION OF INVENTION

Figure 1:
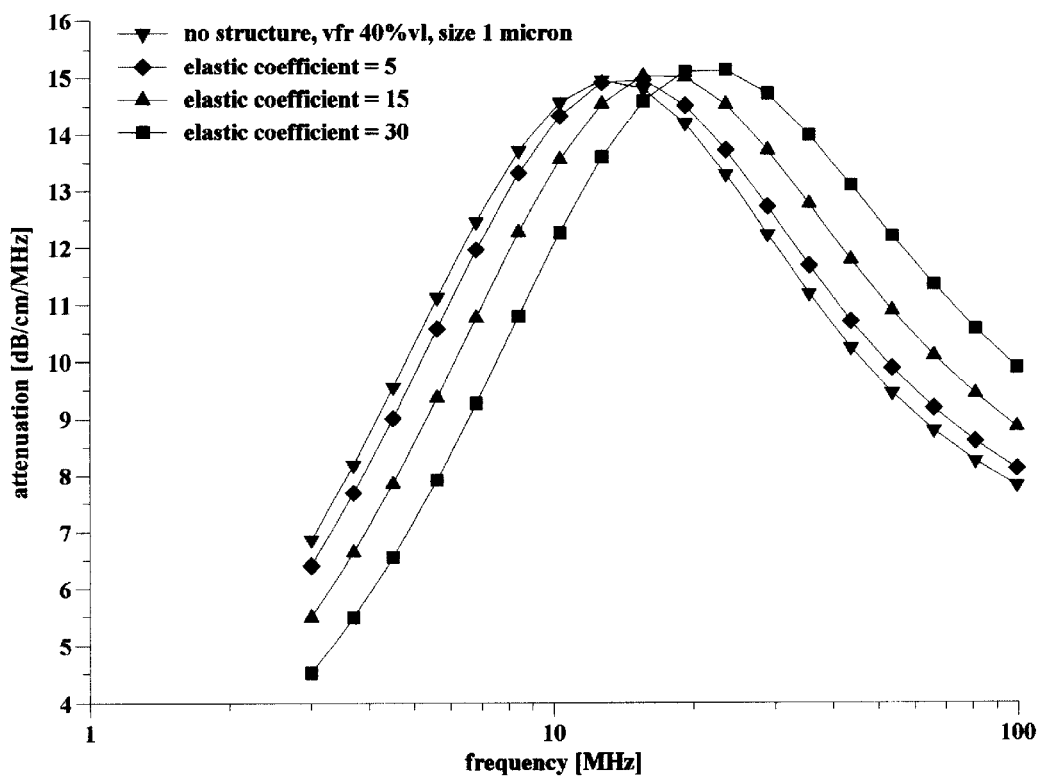
FIG. 1. Theoretical attenuation of the 40%vl alumina slurry with 1 micron particles at different values of the first virial coefficient assuming the second virial coefficient to be a zero.

The biggest advantage of acoustic spectroscopy over most other methods for determining particle size is the ability to characterize concentrated dispersed systems without dilution. The frequency dependence of the sound attenuation and the sound speed are the normal experimental output of this acoustic spectroscopy. Under many conditions, these frequency spectra can then be analyzed in terms of a particle size distribution.

This analysis procedure requires a theory for sound propagation through the dispersed system There already exists such a theory for concentrated dispersions of sub-micron particles with a high density contrast [A. S. Dukhin and P. J. Goetz, "Acoustic Spectroscopy for Concentrated Polydisperse Colloids with High Density Contrast", Langmuir, 12 [21] 4987–4997, 1996.]. This theory takes into account hydrodynamic particle-particle interaction, which is important for the viscous component of the sound attenuation. In addition, this theory also describes the contribution of specific forces which are modeled as flexible strings connecting the particles. This second contribution is here for the first time called "structural losses".

This additional mechanism of sound attenuation complicates the characterization of the particle size distribution. Fortunately, in many cases structural losses are negligible even at very high volume fractions. For instance, experimental dilution tests with concentrated dispersions of both rutile and silica yield correct particle size taking into account only these viscous losses [Dukhin, A. S., Shilov, V. N, Ohshima, H., Goetz, P. J "Electroacoustics Phenomena in Concentrated Dispersions. New Theory and CVI Experiment", Langmuir, 15, 20, 6692–6706, 1999].

However, we can point to other instances where including only the viscous losses in the theory fails to fit the experimental data. One such example is given in a paper by several Japanese scientists [Hayashi, T., Ohya, H., Suzuki, S., Endoh, S., "Errors in Size Distribution Measurement of Concentrated Alurnina Slurry by Ultrasonic Attenuation Spectroscopy", J.Soc. Powder Techn., Japan, 498–504 (2000)]. We will use the data from this paper to show that this new structural loss mechanism provides the required theoretical framework for more completely characterizing the attenuation spectra in structured systems.

There are now a total of six known mechanisms of interaction between sound and a dispersed colloidal system: 1) scattering; 2) viscous; 3) thermal; 4) intrinsic; 5) electrokinetic; and 6) this new structural loss. Except for scattering mechanisms involve converting the acoustic energy to heat. In this work we consider only the viscous, intrinsic and structural loss mechanisms, because these three mechanisms alone are sufficient for fully characterizing the propagation of sound through dispersions of particles having high density-contrast and a diameter less than 3 microns.

The viscous losses occur due to a relative motion occur between the particle and the surrounding viscous media due to the shear wave generated by the particle oscillating in the acoustic pressure field. These shear waves appear because of the difference in the densities of the particles and medium. This density contrast causes a particle motion with respect to the medium. As a result the liquid layers in the particle vicinity slide relative to each other. This sliding non-stationary motion of the liquid near the particle is referred to as "shear wave".

The intrinsic losses of the acoustic energy occur due to the interaction of the sound wave with the materials of both the particles and the medium, taken as homogeneous phases, i.e. ignoring the particulate nature of the colloid.

The oscillation of the network of inter-particle links in a structured dispersed system causes structural losses. Thus, this mechanism is specific for structured systems.

The coupled phase theory for viscous and structural losses is based on balancing the forces on both the particles and the liquid as well as applying the law of conservation of mass. These force balance equations should take into account both "specific" forces [Lyklema, J. "Fundamentals of Interface and Colloid Science", Volumes 1, Academic Press, 1993] as well as the hydrodynamic forces. Specific forces act like non-ideal springs connecting the particles, following the general transient-network theory created in the works [Chen, M. And Russel, W. B. "Characteristics of Flocullated Silica Dispersions", J.Colloid Interface Sci., 141, 2, 564–577 (1991)]. The simplified version of this model allows one to calculate the complex wave-number.

Two terms are necessary to adequately describe the contribution of these non-ideal springs to the force balance. First term is a Hooke's force proportional to the displacement of the particle with a coefficient $\beta$. The second term is a dissipative force proportional to the particle velocity with a coefficient $\delta$. We assume here that the coefficients $\beta$ and $\delta$ are the same for all particles, a logical first step in incorporating structural effects in the theory of sound propagation through an admittedly polydisperse system.

The resulting expression for the complex wave-number 1 is:

$$\frac{l^2 K^*}{\omega^2} = \frac{(1-\varphi)(\rho_0 + \sum_{i=1}^{N} \frac{\gamma_i(D_i - j\omega\gamma_i)}{j\omega D_i})}{\left[1 - \varphi + \sum_{i=1}^{N} \frac{j\omega\varphi_i\gamma_i}{D_i}\right]^2 - \sum_{i=1}^{N} \frac{\omega^2\varphi_i^2}{D_i}\left[(1-\varphi)\rho_0 + \sum_{i=1}^{N} \frac{\gamma_i(D_i - j\omega\gamma_i)}{j\omega D_i}\right]} \quad (1)$$

where:

$D_i = -\omega^2 \rho^i_p \psi_i + j\omega\gamma_i + j\omega\delta + \beta$ $\gamma = 9\eta\psi_2\Omega$ $F_h = 6\pi\eta a\Omega\mu_p$ and furthermore, where K* is a bulk modulus, the reciprocal of compressibility, $\omega$ is a frequency of sound, $\psi$ is the volume fraction of the disperse phase, j is imaginary unit, a is particle radius, $\eta$ is dynamic viscosity, $\rho_o$ and $\rho_p$ are the density of the media and particle respectively, the index i corresponds to the ith fraction of the particle size distribution, and $\Omega$ is a Stoke's drag coefficient calculated from the separate hydrodynamic problem described in the paper [A. S. Dukhin and P. J. Goetz, "Acoustic Spectroscopy for Concentrated Polydisperse Colloids with High Density Contrast", Langmuir, 12 [21] 4987–4997, 1996.].

The attenuation of ultrasound $\alpha$ and sound speed V are related to the complex wave-number with the following expressions:

$$\alpha = Im(l) \quad (2)$$

$$V = \omega/Re(l) \quad (3)$$

Expression 1 is more general than the original "coupled phase theory". It is valid for a polydisperse system, which is rather important since practical systems might be polydisperse not only in size but also with respect to density or perhaps other physical properties.

Expression 1 can be viewed from two extreme, but useful perspectives.

In the first case we view the dispersion as solid particles connected by zero-mass yet non-ideal springs. This would be appropriate for discussing, for example, the structure induced by polymer bridging in a concentrated dispersion.

Alternatively, we might view the dispersion as consisting of zero-mass particles connected by a similar network in which the volume fraction ($\psi$ described above refers to the gel itself, not that of the particles. Such an interpretation yields a useful expression for describing the complex wave-number in a pure gel. The attenuation of the gel is caused only by the oscillation of the polymer network, or in our terminology it is pure "structural losses". By assuming that the drag coefficient $\gamma$ is equal to zero in Equation 1, we obtain the following expression useful for a pure gels:

$$\frac{l^2 K^*}{\omega^2} = \frac{\rho_0(\beta - \omega^2 \rho_p \varphi) + j\omega\delta\rho_0}{[(1-\varphi)(\beta - \omega^2 \rho_p \varphi) - \omega^2 \varphi^2 \rho_0] + j(1-\varphi)\omega\delta} \quad (4)$$

This expression can be used for calculating the attenuation and sound speed in pastes and gels. It has not yet been tested experimentally. It is seen that attenuation occurs only when the loss coefficient $\delta$ is not zero.

Figure 2:
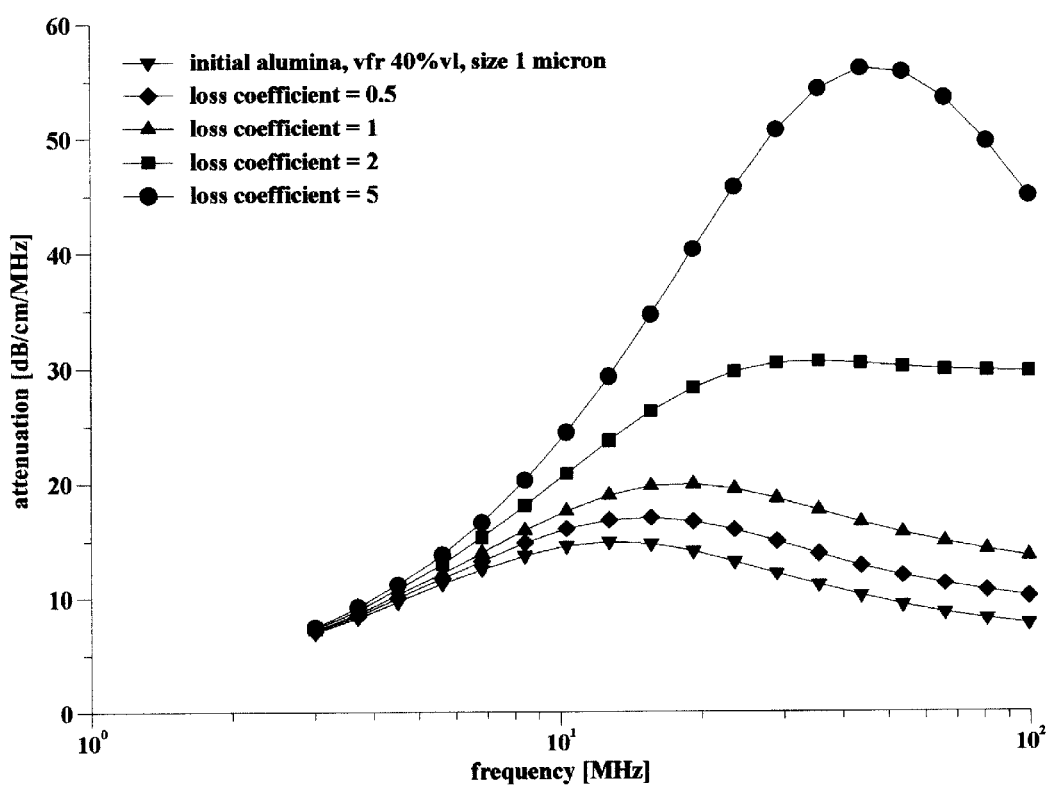
FIG. 2. Theoretical attenuation of the 40% vl alumina slurry with 1 micron particles at different values of the second virial coefficient assuming the first virial coefficient to be a zero.

FIGS. 1 and 2 illustrate the effect of the structure on the attenuation spectra of a 40%vl alumina dispersion with a median size of 1 micron. It is seen that the value of the elastic coefficient $\beta$ just shifts the critical frequency, while keeping the shape of the curve and the maximum attenuation value almost constant. Since the particle size is reciprocally proportional to the square root of this critical frequency, the influence of the structure must be very substantial in order to create large errors in the particle size.

Since the elastic component of the structure does not change the average amplitude of attenuation, only the position of the peak, it is unlikely to effect explain the excess attenuation observed. Such excess attenuation can be explained only by postulating a value for the loss coefficient $\delta$, as follows from FIG. 2.

In principle, this loss coefficient $\delta$ can be automatically extracted from the attenuation spectra, by simply making it an adjustable parameter that is optimized by adjusting the value till the fitting error between the experimental spectra and the predicted spectra is minimized.

We illustrate this method for automatic determination of the loss coefficient $\delta$ using experiments performed at the National Institute for Resources and Environment, Tsukuba, Japan [Hayashi T., Ohya, H., Suzuki, S., Endoh, S., "Errors in Size Distribution Measurement of Concentrated Alumina Slurry by Ultrasonic Attenuation Spectroscopy", J.Soc. Powder Techn., Japan, 498–504 (2000)]. They used two alumina powders: Showa Denko AL-160SG-4 and Sumitomo Chemical Industry ALM-41-01. The median size of the each powder was measured by laser diffraction using a Sympatec Helos and also by photo-centrifugation using a Horiba CAPA-700. These data are summarized in Table 1.

Figure 3:
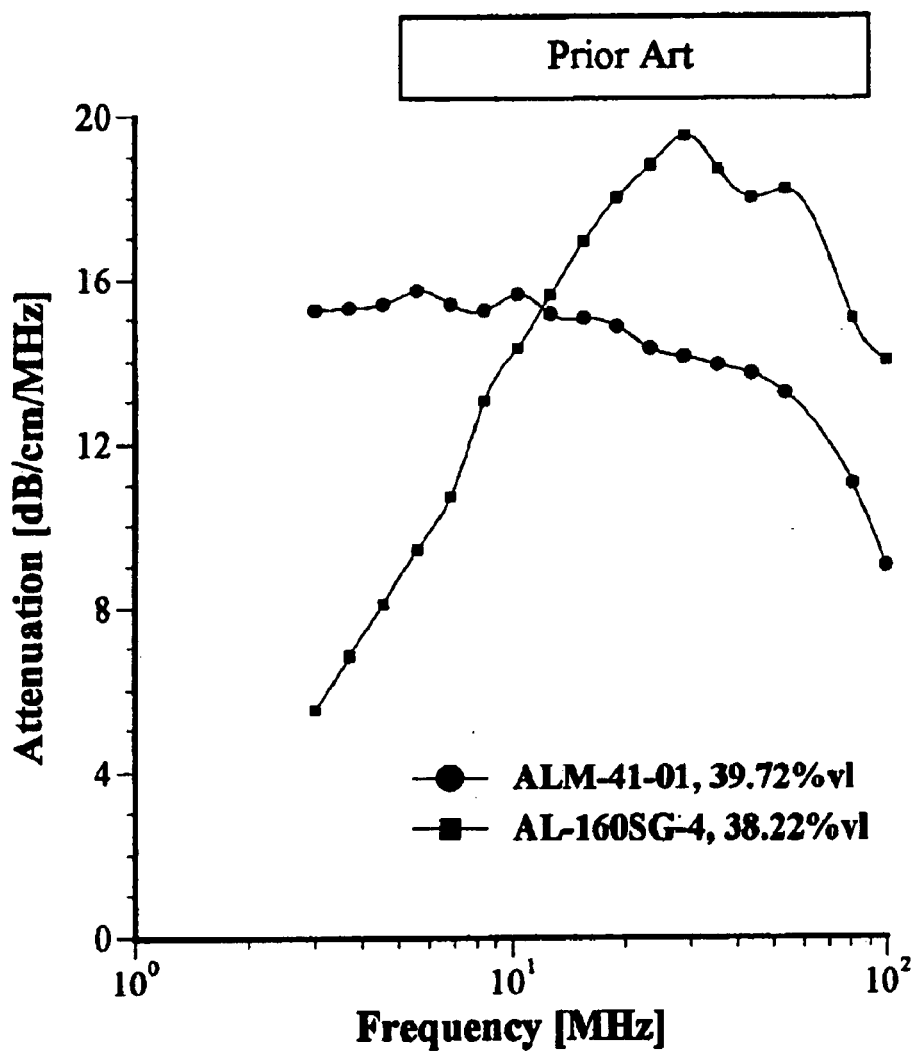
FIG. 3. Experimental attenuation spectra of the two alumina slurries characterized in the paper Hayashi, T., Ohya, H., Suzuki, S., Endoh, S., "Errors in Size Distribution Measurement of Concentrated Alumnina Slurry by Ultrasonic Attenuation Spectroscopy", J.Soc. Powder Techn., Japan, 498–504 (2000).

Both samples were stabilized with sodium polycalboxyl acid as a surfactant and ball milled for 3 days. The volume fractions of the slurries varied from 1% to 40%. They used a PenKem Acoustophor 8000 for measuring the acoustic attenuation spectra of these slurries. The particle size calculated from these attenuation spectra agreed with independent measurements at volume fractions below 20%, as also summarized in Table 1. The attenuation at the highest volume fraction is shown in FIG. 3. We have reproduced these curves from the published graphs because the numerical data was not available in their paper. As a result, one may assume some small deviations from the original data. We have used only the data for the highest volume fraction in the following discussion.

Figure 4A:
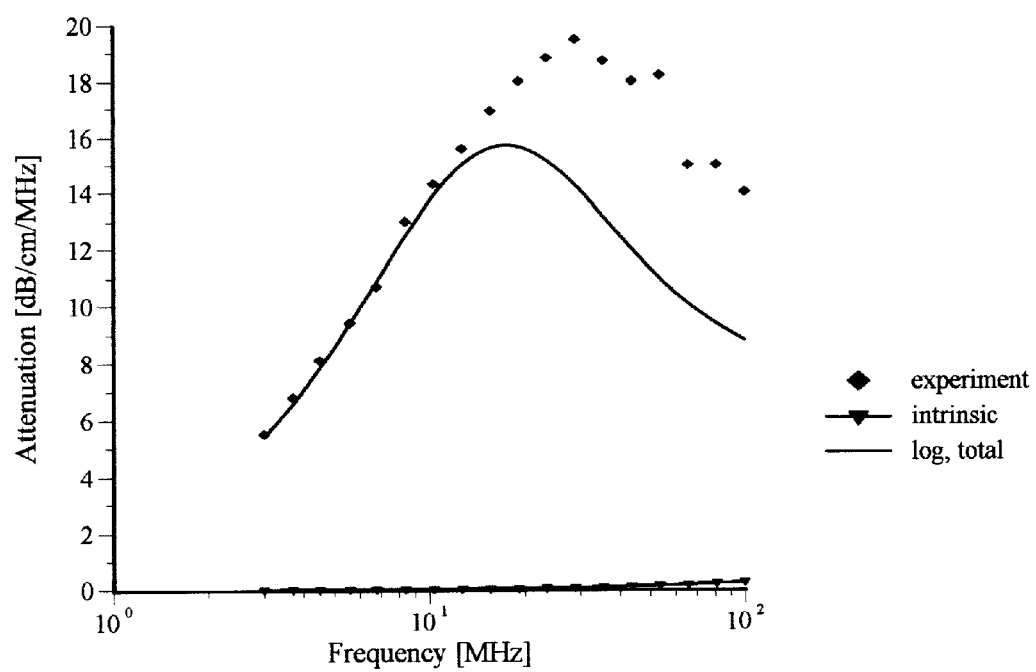
FIG. 4. Theoretical fit to the experimental data presented on FIG. 3 with (b) and without (a) structural losses.

FIGS. 4a shows the experimental and theoretical attenuation spectra at 40% vl for one of the alumina samples. It is seen that the existing theory does not fit the experimental data very well since the experimental attenuation exceeds the theoretical predictions by a substantial degree. Based on this excess, the authors concluded that there is an unknown factor that becomes significant at high volume fraction.

We suggest these "structural losses" as this hypothetical factor. We used Equation 1 to re-calculate the theoretical attenuation spectra. We assumed that the elastic coefficient $\beta$ was zero and made the loss coefficient $\delta$ an adjustable parameter (in addition to the usual lognormal particle size distribution parameters, i.e. median size and standard deviation). The analysis program then looks for the particle size distribution that generates the best fit between the predicted theoretical attenuation spectra and the experimental spectra.

Figure 4B:
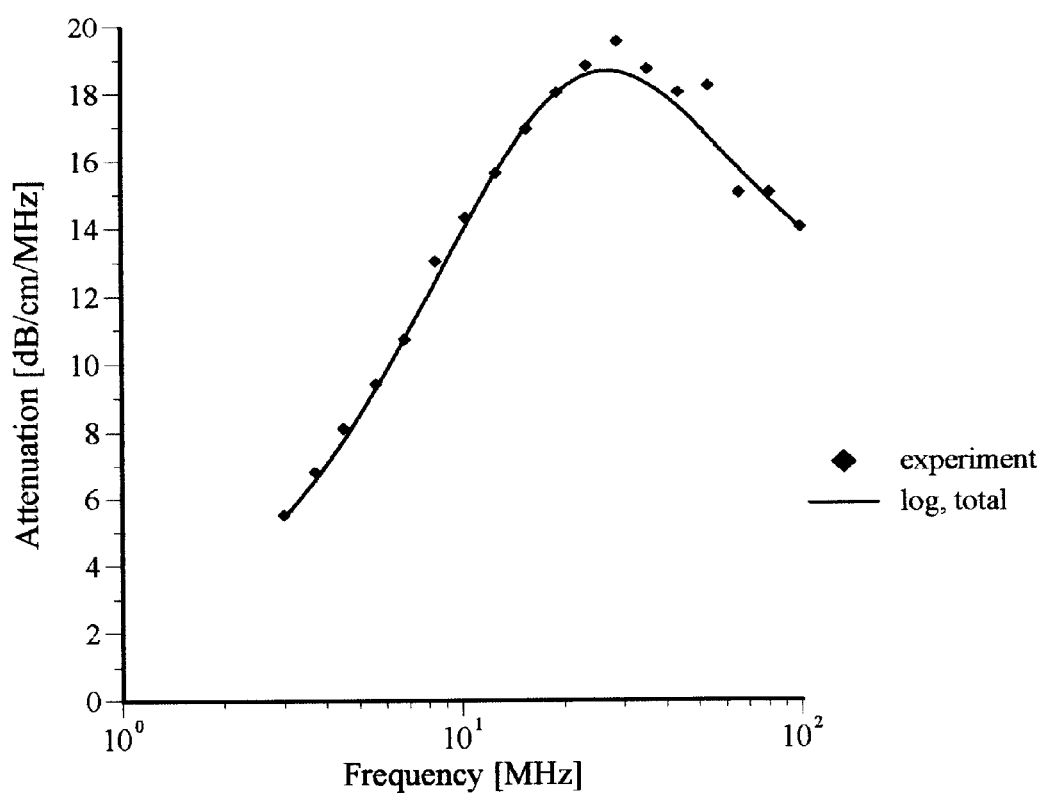

The addition of this new adjustable parameter, $\delta$, allowed us to achieve a much better theoretical fit as illustrated in FIG. 4b. Table 1 gives the results of the calculated particle sizes and fitting errors. It is seen that the addition of this structural loss leads to dramatic improvements in the fitting error, which strongly suggests that this mechanism can indeed explain the observed excess attenuation.

The particle size data confirms this conclusion as well. It is seen that the particle size calculated including these structural losses are much closer to independent measurement performed with diluted system using light based instruments.

It is encouraging to note that the computed value of the loss coefficient $\delta$ turned out to be 0.8 for both samples, in spite of the fact that the particle size was quite different. It seems quite reasonable that the structure should be independent of the particle size, since this parameter characterizes the rheological losses in the polymer chains linking particles together and should be independent of the particles themselves.

We would like to finish with a warning, that the addition of they structural losses to the analysis of attenuation spectra seems justified only when traditional theory fails and experiment shows an excess attenuation. This excess attenuation is then a source of experimental information for calculating micro-rheological properties.

TABLE 2

Particle size of the two alumina samples

| | Median particle size [micron] | |
|---|---|---|
| | ALM-41-01 | AL-160SG-4 |
| Size, Horiba | 1.47 | 0.56 |
| Size, Sympatec | 1.98 | 0.71 |
| Size, PenKem, vfr < 20% | 1.79 | 0.52 |
| Size, Acoustics, vfr = 40% with structural losses | 1.63 (fit error 6.1%) | 0.77 (fit error 2.3%) |
| Size, Acoustics, vfr = 40% no structural losses | 1.07 (fit error 19.2%) | 0.8 (fit error 18.4%) |

What is claimed is:

1. A method of characterizing the micro-rheological properties, as well a more accurate particle size distribution, of structured concentrated dispersions of finite mass particulates, having some interparticle connections, and comprising the steps of:
   measurement of the ultrasound attenuation spectra of the dispersion using prior art;
   employing a prediction theory which estimates the attenuation spectra based not only on the prior art parameters of the particle size distribution, but now augmented to include the viscoelastic properties of the interparticle links between the particles;
   utilizing an analysis engine to automatically adjust not only the parameters of the particle size distribution, but in addition viscoelastic properties, to determine the optimum values of these parameters that achieve the best fit between the measured attenuation spectra and that predicted by this augmented theory;
   and finally using these optimum values for characterizing both the particle size distribution and the viscoelastic properties of the links between the particles.

2. A method of characterizing only the micro-rheological properties of structured concentrated dispersions, where the particle size is known, comprising the steps of:
   measurement of the ultrasound attenuation spectra of the dispersion using prior art;
   employing a prediction theory which estimates the attenuation spectra based not only on the prior art parameters of the particle size distribution, but now augmented to include the viscoeleastic properties of the interparticle links between the particles;
   utilizing an analysis engine to automatically adjust only the viscoelastic properties, to use the known particle size distribution, and to determine the optimum values of only the viscoelastic properties that achieve the best fit between the measured attenuation spectra and that predicted by this augmented theory;
   and finally using these optimum values for characterizing the viscoelastic properties of the links between the particles.

3. A method of characterizing the micro-rheological properties of pure gels, comprising the steps of:
   measurement of the ultrasound attenuation spectra of the dispersion using prior art;
   employing a prediction theory which estimates the attenuation spectra based on the viscoelastic properties of the interparticle links between the particles;
   utilizing an analysis engine to automatically adjust only the viscoelastic properties, and to determine the optimum values of only the viscoelastic properties that achieve the best fit between the measured attenuation spectra and that predicted by this augmented theory;
   and finally using these optimum values for characterizing the viscoelastic properties of the links between the particles.

* * * * *